United States Patent [19]

Janu et al.

[11] 4,163,929
[45] Aug. 7, 1979

[54] HANDLE APPARATUS FOR A POWER-ASSIST DEVICE

[75] Inventors: Maria M. Janu, Brookfield; Howard R. Wagner, Milwaukee, both of Wis.

[73] Assignee: General Electric Company, Milwaukee, Wis.

[21] Appl. No.: 929,001

[22] Filed: Jul. 28, 1978

[51] Int. Cl.² .............................................. G05B 11/01
[52] U.S. Cl. .................................... 318/628; 318/657; 250/449
[58] Field of Search .......................... 318/628, 657, 2; 250/449, 525

[56] References Cited

U.S. PATENT DOCUMENTS

| | | | |
|---|---|---|---|
| 3,866,048 | 2/1975 | Gieschen et al. | 250/449 |
| 4,021,715 | 5/1977 | Von Hacht et al. | 318/628 |
| 4,107,590 | 8/1978 | Pury et al. | 318/628 |

*Primary Examiner*—B. Dobeck
*Attorney, Agent, or Firm*—Roger C. Turner

[57] ABSTRACT

A handle apparatus is for use with a device which has a movable component and a variable speed motor system which is responsive to an error signal for driving the movable component to desired positions corresponding to the error signal. The handle apparatus includes a central stationary support member which can be mounted to the movable component. The support member is adapted to receive a miniature force sensor which includes a linear variable differential transformer having an operative axis. The member receives one force sensor for each axis in which power-assist is desired; with the axis of each force sensor positioned corresponding to each axis of power-assist. Each force sensor is electrically connected to an input signal and has an actuator translatable along the operative axis connected to a central core and has a base containing the transformer wherein movement of the actuator translates the core within the transformer to produce the error signal corresponding to the magnitude and direction of the translation of the core. A generally hollow, cylindrical sleeve encloses the support member and the force sensors to form a manually engageable surface. The sleeve is adapted to independently engage each actuator of the force sensors. Each actuator of the force sensors operates through a spring diaphragm which positions and returns the sleeve to a stable position and provides elastic resistance to force in any direction. Any manual force applied to the sleeve translates the corresponding actuator to thus produce the error signal which is proportional to the magnitude and direction of the force.

7 Claims, 6 Drawing Figures

HANDLE APPARATUS FOR A POWER-ASSIST DEVICE

BACKGROUND OF THE INVENTION

This invention relates generally to a handle apparatus for a power-assist device where it is desired to cause a motor to position a heavy object in response to a small manual force being applied to the handle. The invention relates particularly to the handle having force sensors which provide a signal to a variable speed motor proportional to the manual force applied to the handle.

Although the device is useful in many kinds of machines, a typical use of the new handle is in an x-ray table which is equipped with a spot-film device. A spot-film device includes a carriage which is mounted in the body of an x-ray table for being moved longitudinally thereof. Supported on the carriage above the table is an enclosure which may be adated for accommodating a film cassette and an x-ray image intensifier. The enclosure is usually mounted on the carriage in such manner that it may be shifted to various positions relative to the x-ray table top.

It is customary to have a manually engageable handle attached to the enclosure. The operator may then grasp the handle and push or pull the enclosure to position it as required. The handle enables the operator to apply force in a longitudinal direction for activating an electric motor that drives the heavy carriage to its desired longitudinal positions. Additional electric motor drives can be provided for moving the carriage to desired vertical and lateral positions.

In some prior art x-ray tables, the operating handle is mounted for pivotting or sliding through a perceptible distance so that when a force is applied, the handle may actuate potentiometers or switches which select motor speed and direction for longitudinal positioning of the spot-film device. In using this prior art system, the operator was deprived of the naturally expected feeling of proportionality between the magnitude of the manually applied force and the rate and direction in which the spot-film device moves. Despite extensive efforts at refinement, in proportional systems where potentiometers or switches are used to initiate driving action, the operator does not get a true sense or feeling of the massive component moving in proportion to the force which is being applied.

The prior art has attempted to proportion the manual force applied to a handle and the rate of the movement by a motor system as shown in U.S. Pat. No. 3,866,048 to Gieschen, et al, which employs a piezo-electric crystal in conjunction with movement of a handle. A piezo-electric crystal is extremely expensive for this application. The crystal is shown between the handle and the equipment with the crystal receiving a force through a bulky lever and linkage mechanism. It is very difficult to isolate force in each separate axis of multi-axis crystals, so there is frequently cross talk between the crystals.

Another prior art system is shown in copending U.S. patent application Ser. No. 733,644 to Pury, et al, now U.S. Pat No. 4,107,590, assigned to the assignee of the present invention, which incorporates a handle operating through a flexure member containing strain gauge transducers to produce a signal which drives a variable speed motor proportional to the forces applied to the handle. The system can provide excellent proportional performance for a specific device; however, the strain gauge transducers are very expensive and delicate, and require complex chemical bonding to a heavy flexure member. The quality of bonding varies from assembly to assembly and results in variable sensitivity and response to an applied force.

The function of the strain gauge and crystal transducers require relatively heavy members for operation and, therefore, requires error correction for the forces of the weight of the handle itself in certain positions.

The function of the strain gauges results in cross talk between adjacent gauges which are intended to respond independently to forces along different axes.

A particular problem with strain gauge transducers is the considerable signal drift during warm-up and during changes in ambient temperature. The assemblies are difficult to calibrate and do not have consistent performance.

Accordingly, one object of the present invention is to provide a handle for a power-assist device which uses inexpensive components which can be easily and repeatably installed.

Another object of the invention is to provide a handle which is compact, housing the force transducers within the handle itself, and which is lightweight requiring no error correction for position.

Still a further object of the present invention is to provide a handle which can be easily zeroed and which has repeatable sensitivity over an extended life during changes in ambient conditions.

SUMMARY OF THE INVENTION

The invention is directed to a handle apparatus for producing an error signal correspondingly proportional to a manual force applied to the handle. The handle is for use with a device which has a movable component and a variable speed motor system which is responsive to the error signal for driving the movable component to desired positions corresponding to the error signal. Such a device is an x-ray fluoroscopic imaging assembly having a drive system as described in the aforementioned U.S. patent application Ser. No. 733,644 to Pury, et al now U.S. Pat. No. 4,107,590. The handle apparatus receives an input signal and contains force sensors which produce an error signal corresponding to the direction and magnitude of force applied to the handle.

In accordance with the invention, the handle apparatus includes a central stationary support member which can be mounted to the movable component. The support member is adapted to receive a miniature force sensor which includes a linear variable differential transformer having an operative axis. The member receives one force sensor for each axis in which power-assist is desired; with the axis of each force sensor positioned corresponding to each axis of power-assist. Each force sensor is electrically connected to the input signal and has an actuator translatable along the operative axis connected to a central core and has a base containing the transformer wherein movement of the actuator translates the core within the transformer to produce the error signal corresponding to the magnitude and direction of the translation of the core. A generally hollow, cylindrical sleeve encloses the support member and the force sensors to form a manually engageable surface. The sleeve is adapted to independently engage each actuator of the force sensors. Each actuator of the force sensors operates through a spring diaphragm which positions and returns the sleeve to a stable position and provides elastic resistance to force in any direction. Any manual force applied to the sleeve translates the corresponding actuator to thus produce the error signal which is proportional to the magnitude and direction of the force.

BRIEF DESCRIPTION OF THE DRAWINGS

While the novel features of the invention are set forth with particularity in the appended claims, the invention will be better understood along with other features thereof from the following detailed description taken in conjunction with the drawings in which:

DESCRIPTION OF THE PREFERRED EMBODIMENT

Figure 1:
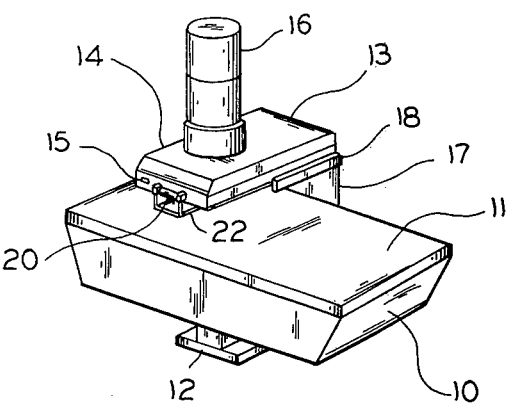
FIG. 1 is a perspective view of a diagnostic x-ray table in which the new handle apparatus may be used.

Referring first to FIG. 1, there is shown a typical diagnostic x-ray table in which the handle apparatus of this invention may be used and includes a main frame 10, having an x-ray permeable patient supporting top 11. The table is mounted on a stand 12 in a conventional manner such that it is subject to being tilted or angulated longitudinally. The table has x-ray imaging apparatus generally designated by the reference numeral 13, for making radiographic films and for electronically amplifying an x-ray image so that it can be displayed on a television monitor, not shown. The imaging assembly comprises a housing 14 which has an opening 15 in its front for admitting and withdrawing a film cassette.

Mounted on top of the housing is an x-ray image intensifier assembly 16. The imaging assembly 13 is carried on a column 17 which is usually made to be vertically extensible and contractable so that the film plane and the image input plane of the intensifier can be established at any desire height. Column 17 is provided with tracks, such as 18, on which the assembly 13 is mounted. Thus, assembly 13 may be manually urged laterally, that is, forwardly and rearwardly as viewed in FIG. 1, to thereby locate it over the table top or to get it out of the way as desired. Column 17 is part of a carriage, not visible, which is mounted in main frame 10 on suitable tracks so that the assembly 13 may be translated longitudinally on the table top 11. The invention contemplates that the assembly 13 and carriage will be translated longitudinally under the influence of an electric motor drive, not shown. Any of the well-known drive systems may be used, such as those which employ a motor, sprockets and chains, or pulleys and cables. Also not shown is the conventional system for counterbalancing the carriage and components carried on it so that the carriage will tend to stay in a fixed position when the table is tilted or angulated from horizontal toward a more vertical attitude.

In accordance with the present invention, the x-ray imaging assembly 13 has a manually engageable handle apparatus 20 fastened to housing 14 by mounting members 22. The handle may be gripped and used by an operator to push and pull imaging assembly 13 for positioning vertically and longitudinally relative to the top 11 of the x-ray table. Handle 20 may also be adapted to bring about lateral positioning of image assembly 13 with the use of a power-assist device, but for the sake of simplicity in describing the basic concepts of the invention, use of the handle in a power-assist system for only vertical and longitudinal movement will be discussed.

Figure 2:
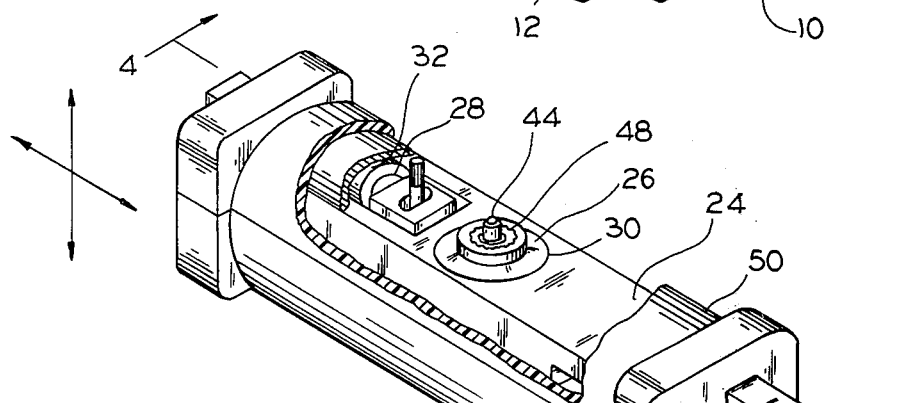
FIG. 2 is an enlarged partially cut-away perspective view of the handle shown in FIG. 1.

Referring to FIG. 2 there is shown the details of the handle apparatus 20. The handle apparatus 20 has a central stationary support member 24 which is fixedly mountable to mounting members 22. The support member houses miniature linear variable differential transformers (LVDT) force sensors 26 and 28. The support member 24 can be suitably formed from a metallic material, such as aluminum, having cavities adapted to fixedly receive the force sensors. In this preferred embodiment, the handle apparatus is designed for a four way power-assist device responding to forces in the vertical and the longitudinally horizontal axes. The LVDT force sensors have a generally cylindrical base and have a central operative axis. The support member 24 has a generally cylindrical vertical cavity 30 for fixedly positioning force sensor 26 and has a generally cylindrical longitudinal cavity 32 for fixedly positioning the base of force sensor 28.

Figure 3:
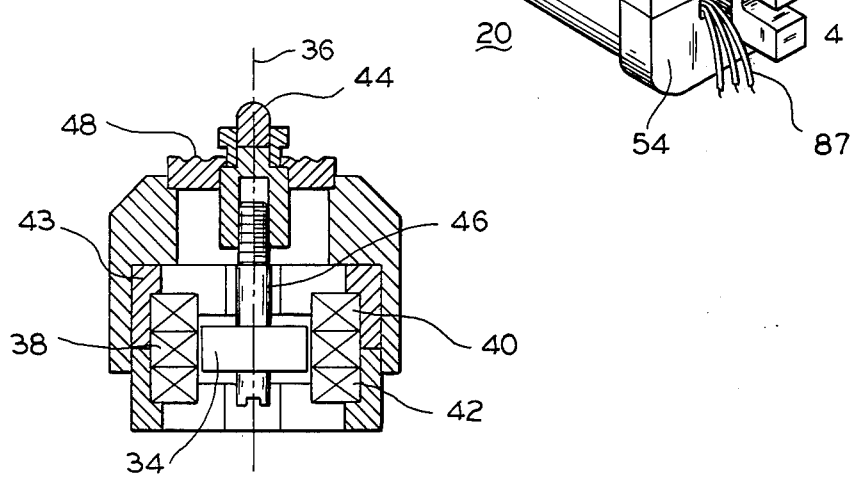
FIG. 3 is a sectional view of the force sensor shown in FIG. 1.

Referring now to FIG. 3, there is shown an enlarged LVDT force sensor, such as 26, which is the operative heart of the invention. The miniature compact packaging of the force sensor permits it to be completely self contained within the handle apparatus. The precise function of the LVDT force sensor permits consistent, repeatable performance which was heretofore not available from an installed transducer. The LVDT is essentially a transformer designed with a high degree of sensitivity to a change in coupling produced by a movement of a magnetic core 34 within a set of windings. The force sensor has a central operative axis 36. A single primary winding 38 receives an input signal and is coupled to a secondary winding 40 positioned directly above and a secondary winding 42 positioned directly below wherein the secondary windings are wound opposite in direction and are connected in series. The windings are enclosed within a Ferrite housing 43. An actuator 44 is connected to core 34 by a shaft 46. With the core in a neutral position, the coupling between each secondary winding and the primary winding is equal and since they are opposed in phase, the secondary windings cancel and the output is zero. As the core 34 is translated in either direction from the neutral position, the coupling to one secondary is increased and the coupling to the other secondary is decreased resulting in an AC output proportional to the translation distance of the core. The phase of the output voltage will be 180° in opposite direction as the core is translated in opposite directions from the neutral position. A suitable LVDT is commercially available from Johnson Controls, Milwaukee, Wis., part No. 27-768-3.

Using a 15 volt input signal and a circuit which will later be discussed, a 0.001 inch downward translation of the core 36 produces a −1.6 volt output, referred to as an error signal. A further downward translation produces an error signal which is precisely linear. Maximum downward translation of 0.005 inches produces an error signal of −8 volts. Similarly, an upward translation of the core produces a precisely linear error signal, up to a maximum of 0.005 which produces an error signal of +8 volts.

The translation and resulting error signal function of the LVDT is correlated into a force sensor by way of an elastic resistance provided by spring diaphragm 48. A suitable spring diaphragm has a diameter of 0.562 inches and a thickness of 0.0045 and is made from beryllium copper, commercially available from Johnson Controls, part number 24-265-2. This particular spring diaphragm 48 reacts linearly to both positive and negative forces to the actuator 44 and has a spring rate of 1000 pounds per inch of deflection. A force of one pound will translate the actuator 0.001 inch and, correspondingly, a five pound force will produce a 0.005 translation. Thus, the error signal produced in secondary windings 40 and 42 will correspond to the direction and be proportional to the force applied to the actuator. Other springs or electric materials can be employed to provide the stabilizing elastic resistance to the LVDT.

Figure 4:
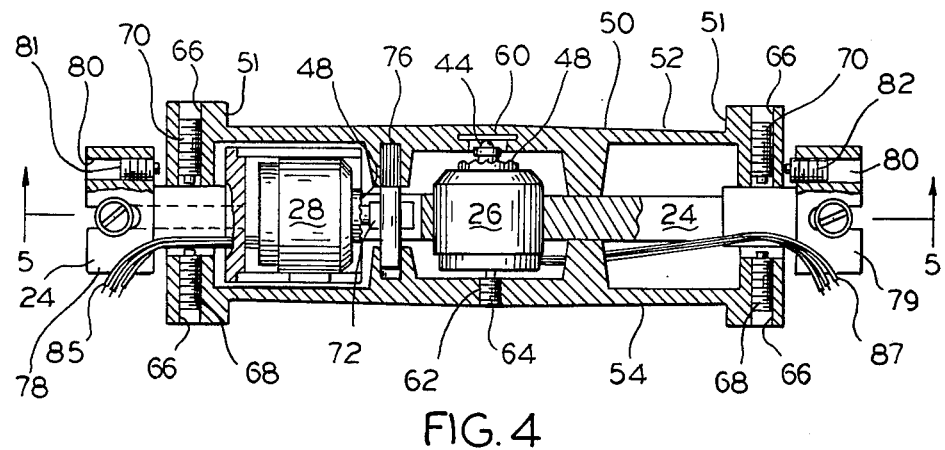
FIG. 4 is a section view taken along line 4—4 of FIG. 2.
Figure 5:
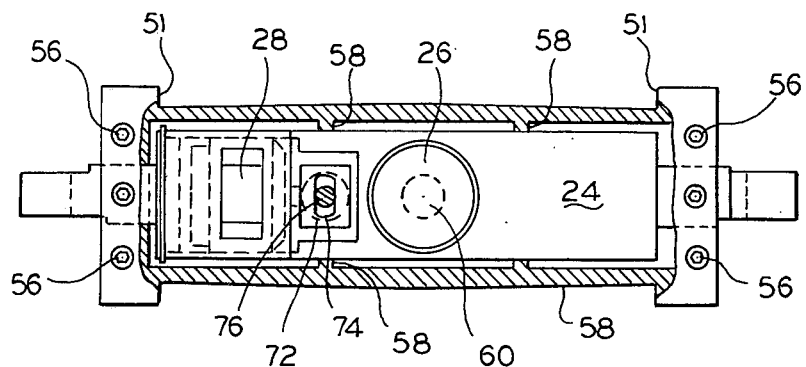
FIG. 5 is a sectional view taken along axis 5—5 of FIG. 4.

Referring particularly to FIGS. 4 and 5, the operation of the handle apparatus 20 can be described. A generally hollow cylindrical sleeve 50 encloses the support member 24 and the force sensors 26 and 28 forming a manually engageable surface. The sleeve is contoured for manual engagement and has smooth radial flanges 51 on both ends to facilitate the application of a longitudinal force. The sleeve is molded as an upper half 52 and a lower half 54 of a suitable material, such as LEXAN ® polycarbonate resin. The upper half 52 and the lower half 54 are adapted to be attached to each other by standard fasteners 56. The inner structure of sleeve 50 is adapted to transmit any force applied to the sleeve to the corresponding actuator of each force sensor. As previously indicated, in other embodiments well known elastic materials could be employed between the sleeve 50 and the support member 24 to provide the stabilizing resistance to the LVDT. The inner structure is contoured to receive the support member 24 in a generally centered position within the two halves of the sleeve. The sleeve 50 includes molded inner members 58 which resist lateral movement of the sleeve on support member 24, but the sleeve is otherwise free to float vertically and longitudinally on the support member with a very tightly controlled clearance.

The upper half 52 of the sleeve 50 contains an inserted stainless steel disc 60 positioned to contact the vertical actuator 44 of force sensor 26. The lower half 54 contains a threaded aperture 62 adapted to receive a recessed threaded pin 64 and positioned so that the pin can contact the bottom of shaft 46 of force sensor 26. During assembly, the error signal of the sensor 26 is monitored while the threaded pin 64 is advanced until the core 34 is contacted, as indicated by the error signal, then using a dial indicator gauge, the pin is retracted 0.004 inches for clearance. Any force having a downward component will cause the disc 60 to translate the actuator 54 and the core 34 to produce the proportional downward error signal; while any force having an upward component will cause the pin 64 to translate the shaft 46 and the core 34 to produce the corresponding proportional upward error signal. The disc 60 has a smooth surface which can move longitudinally relative to the actuator 44 with no translation of the actuator.

Since the power-assist system of this preferred embodiment is fully actuated by a force of 5 pounds, and the spring diaphragm 48 is subject to being over stressed, threaded apertures 66 and adjustable lower stops 68 and upper stops 70 are provided to limit the relative vertical travel of sleeve 50. An 8 pound load is suspended from sleeve 50 while the error signal is monitored. The lower stops 68 are advanced into the apertures until they contact the support member 24 as indicated by a change in the error signal. The handle is then turned over, the 8 pound weight is suspended and the upper stops 70 are similarly adjusted so that force sensor 26 and diaphragm 48 cannot be subjected to a force exceeding 8 pounds.

The longitudinal force sensor 28 operates exactly as force sensor 26 except that it has an actuator lug 72 to translate the core 34. The actuator lug 72 has a slotted hole 74 adapted to receive an actuator pin 76. The pin 76 is vertically positioned fixedly between sleeve halve 52 and half 54 and extends through the slotted hole. The hole 74 and pin 76 are sized so there is 0.004 inches of clearance in the longitudinal direction and approximately 0.060 inches of clearance in the lateral direction. If a force having a leftward longitudinal component is applied to sleeve 50, the pin 76 will cause actuator lug 74 to translate the core 34 to the left. The actuator 74 also acts through another spring diaphragm 48 so that the error signal produced by the translation of the core is proportional to the force applied to the sleeve. If a rightward longitudinal force is applied to the sleeve, the pin 76 will cause the lug 74 to translate core 34 to the right, to produce an error signal opposite in phase and proportional to the force applied to the sleeve. It can be easily seen that any vertical force on sleeve 50 and resulting movement of the sleeve 50 will cause the pin to just slide vertically within the slotted hole 74 without any longitudinal translation of force sensor 28. The sleeve 50 independently engages the actuator 44 and actuator lug 72 of the force sensors with no cross talk of error signals between the respective force sensors.

Longitudinal movement of the sleeve 50 relative to support member 24 is restricted to protect the force sensor 28 and its spring diaphragm 48 from being over stressed. The ends 78 and 79 of support member 24 which extend beyond sleeve 50 have threaded longitudinal apertures 80 adapted to receive adjustable stops 81 and 82. During assembly, the support member 24 is suspended by end 79 and an 8 pound weight is suspended from sleeve 50. The error signal from force sensor 28 is monitored while adjustable stop 81 is advanced until a change appears in the error signal. The member 24 is then suspended from the other end 78 and adjustable stop 82 is similarly adjusted so that the force sensor 28 and diaphragm 48 cannot be subjected to a force exceeding 8 pounds. The electrical wire connections 85 and 87 for the force sensors extend out of the ends between sleeve 50 and support member 24.

The light weight, nonmetallic sleeve 50 does not exert enough weight on the force sensors to initiate an error signal irrespective of the position of the handle. Therefore, the handle requires no circuitry for error correction for position and is a significant improvement over the prior art.

Figure 6:
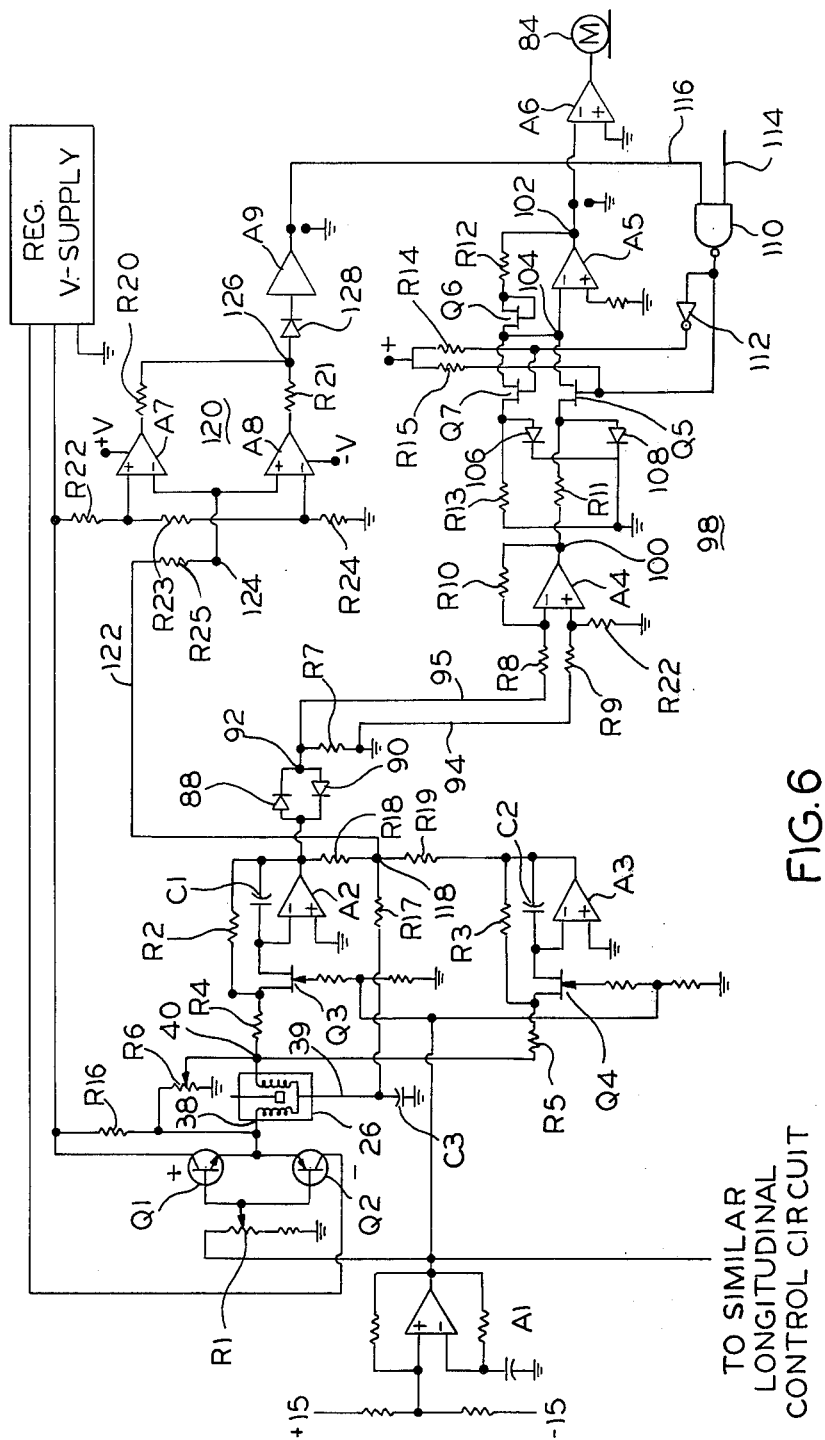
FIG. 6 is an electric circuit diagram for the handle apparatus power-assist system.

Refer now to FIG. 6 for a discussion of the electrical features of the power-assist system. A motor 84 for vertically driving the carriage which supports the image assembly 13 of the x-ray table is shown at the far right of the drawing. The mechanical coupling between the motor and the carriage in the x-ray table is not shown since it is conventional.

Near the left of FIG. 6 is shown the LVDT force sensor 26 installed to cause the motor 84 to drive the carriage when subjected to a vertical force on the handle. Only the vertical channel is shown, but a similar circuit is incorporated with force sensor 28 to drive the carriage in the direction of a longitudinally applied force on the handle.

An oscillator A1 network is shown to the far left of the circuit. The oscillator A1 provides a ±15 volt, 16 KHz square wave input voltage signal to the system. The signal is delivered through a gain adjustment potentiometer R1 and through output transistors Q1 and Q2 to the primary winding 38 of the force sensor 26. The output of the secondary winding 40 of the force sensor is connected to the input of two amplifiers A2 and A3. The inputs of the amplifiers A2 and A3 are gated on opposite phases of the oscillator A1 by two field effect transistors (FETs) Q3 and Q4. When the FETs Q3 and Q4 are alternately turned on, the input signal from the force sensor charges capacitors C1 and C2 between each amplifier output and the inverting input. The capacitors C1 and C2 hold the charge when the FETs are off. Overall DC gain of each amplifier is set by the feedback resistors R2 and R3, in conjunction with resistors R4 and R5.

The force sensor is zeroed by adjustable potentiometer R6. With no force applied to force sensor 26, the potentiometer R6 is adjusted for zero output from amplifier A2. The system is calibrated by applying a force of 5 pounds to force sensor 26, then adjusting gain adjustment potentiometer R1 until the output from amplifier A2 is 8 volts.

The purpose of the amplifier A3 is to act as a summing or averaging amplifier for comparison to amplifier A2 to facilitate detection of any circuit malfunction within the system, which will be discussed later.

A pair of oppositely poled diodes 88 and 90 require an output signal from amplifier A2 which is above their forward threshold voltage. Thus the diodes provide a small dead band before motor 84 is caused to turn in one direction or the other.

When the handle is urged upward, an error signal of increasing magnitude is produced at point 92 and when urged downward, a decreased voltage or error signal having opposite polarity is developed at point 92. The error signal, after processing, is used to cause motor 84 to be drive in one direction or another at a rate depending on the magnitude and polarity of the error signal at point 92. The error signal at 92 developes a voltage signal across R7 connected between the output and ground. The voltage signal developed across R7 is supplied over lines 94 and 95 through input resistors R8 and R9 to the inverting and noninverting inputs of a differentially connected operational amplifier A4. This amplifier has the customary feedback resistor R10 connected between its input and output for setting gain.

Operational amplifier A4 is a differential line receiver acting as the input stage to a signal conditioning circuit 98. Error signals from amplifier A4 are delivered from its output terminal 100 through a resistor R11 and a serially connected FET Q5 to the inverting input of another operational amplifier A5. The output signal having polarity corresponding with the error signal at output terminal 102 of amplifier A5 is supplied to the inverting input terminal of a servo amplifier A6 which has its noninverting input connected to ground. The output from amplifier A6 causes motor 84 to be driven in one direction or another depending on the polarity of the input error signals developed at point 92 in the first stage of the system. Amplifier A5 has a feedback circuit including a resistor R12 in series with a FET Q6 and a jumper 104 which results in the feedback circuit being connected between the output 102 and the inverting input of amplifier A5. A series circuit including a FET Q7 and a resistor R13 is connected from the feedback circuit to ground. Diodes 106 and 108 and pullup resistors R14 and R15 are provided to cause the proper bias voltage to be applied to FETs Q5 and Q7. Resistors R11 and R13 preferably have equal values. The gates of FETs Q5 and Q7 are controlled by the condition of the output signal of a NAND gate 110. The output of NAND gate 110 is coupled to the gate of transistor Q7 through an inverter 112. It will be evident that when the output of NAND gate 110 goes high, field effect transistor Q5 will turn off and, due to inverter 112, transistor Q7 will turn on. When the outut of NAND gate 110 is low, Q5 will be turned on and Q7 will be off. In other words, when either Q5 or Q7 is on, the other will be off.

NAND gate 110 has two inputs, 114 and 116. The state of inputs 114 and 116 determines whether the power-assist system is to be inactivated or allowed to operate in its normal fashion. It will be evident that when both inputs 114 and 116 to gate 110 are high, the output of the gate will be low in which case Q5 will be on and Q7 will be off. On the other hand, if either or both inputs 114 and 116 are low, the output of gate 110 will be high and Q5 will be turned off. If Q5 is off, the error signal is not applied to the input of amplifier A5 and servo motor amplifier A6 will have no input so the drive motor 84 for the x-ray table carriage cannot drive. If no error signal exists, of course, as is the case when no manual force is being applied to the operating handle, servo amplifier A6 remains nulled and motor 84 does not drive.

Input 116 of NAND gate 110 may also handle a signal which when low, will deactivate motor 84 and which when high in conjunction with input 114 being high will allow the motor to run in response to the handle being urged vertically. Both inputs 114 and 116 must be high for motor 84 to be operated.

Another significant feature of the system is the provision of means for deactivating the drive motor 84 in case of failure of the LVDT force sensor or the electronic circuit which might result in an error signal being produced without any force being applied to the operating handle. The LVDT primary 38 is returned to ground along line 39 through a capacitor C3. The capacitor C3 isolates the voltage in the LVDT for use in the failure detection circuit. The primary 38 is also connected to the power supply through R16 to provide a detectable current at a summing network 118. The output from amplifiers A2 and A3 and the LVDT are combined at the summing network 118 formed by resistors R16, R17, R18 and R19. Any change in a predetermined current through the summing network 118 is sensed with a window comparator 120. The comparator 120 comprises a pair of operational amplifier A7 and A8 which have resistors R20 and 21, respectively, in series with their outputs. The reference voltage for the comparator is obtained with a voltage divider comprised of resistors R22, R23 and R24. Intermediate points of the divider are connected to the noninverting input of amplifier A7 and to the inverting input of amplifier A8 as shown. An error signal resulting from an electronic failure or LVDT failure and a change in current is applied through R25 by means of line 122. The voltage at point 118 will have a predetermined value of 5 volts as long as the circuits and the LVDT are operating properly. However, if a circuit element failure occurs, there will be a substantial change in voltage at 118 and this will be sensed as a voltage change at the intermediate point 124. If the voltage change is outside of the window of comparator 120, the comparator will change state and cause the output signal at junction 126 to switch from high to low. This signal is transmitted through a diode 128 to a buffer amplifier A9 whose output will also switch from high to low. This means that the input 116 of NAND gate 110 will go from high to low and the output of the gate will go high. Upon this event, Q5 will turn off as explained earlier and amplifier A5 and servo amplifier A6 for the motor 84 will be deactivated in which case the carriage in the x-ray table will be held in a fixed position.

The handle apparatus described above provides a low cost, light weight compact reliable handle for a power-assist device.

While a specific embodiment of the present invention has been illustrated and described herein, it is realized that modifications and changes will occur to those skilled in the art. It is, therefore, to be understood that the appended claims are intended to cover all such modifications and changes as fall within the true spirit and scope of the invention.

What is claimed is:

1. A handle apparatus havng an input signal and producing an error signal for use with a device which has a movable component and variable speed motor means which is responsive to the error signal operatively connected to the component for driving it to desired positions corresponding to the error signal, wherein said handle apparatus is manually engageable and subject to having a manual force applied substantially in the direction in which movement of said component is desired, said handle apparatus comprising:

a central stationary support member having means for being fixedly mounted to the component, said support member being adapted to receive a miniature force sensor which includes a linear variable differential transformer having an operative axis, said member having one said force sensor for each axis in which power-assist is desired with the axis of each said force sensor positioned corresponding to each axis in which power-assist is desired, said force sensor being electrically connected to the input signal and having an actuator translatable along the operative axis connected to a central core, and having a base containing the transformer wherein movement of said actuator translates the core within the transformer to produce the error signal corresponding to the magnitude and direction of the translation of the core, a generally hollow cylindrical sleeve, enclosing said support member and each said miniature force sensor, forming a manually engageable surface, means for said sleeve to independently engage each said actuator, and means for positioning and returning said sleeve to a stable position and having elastic resistance to force in any direction whereby any said manual force applied to said sleeve translates said actuator to thus produce said error signal which is proportional to the magnitude and direction of said force.

2. A handle apparatus having an input signal and producing an error signal for use with an x-ray device which has a movable image component and variable speed motor means which is responsive to the error signal operatively connected to the component for driving it to desired positions corresponding to the error signal, wherein said handle apparatus is manually engageable and subject to having a manual force applied substantially in the direction in which movement of said component is desired, said handle apparatus comprising:

a central stationary support member having means for being fixedly mounted to the component, said support member being adapted to receive a miniature force sensor which includes a linear variable differential transformer having an operative axis, said member having one said force sensor for each axis in which power-assist is desired with the axis of each said force sensor positioned corresponding to each axis in which power-assist is desired, said force sensor being electrically connected to the input signal and having an actuator translatable along the operative axis connected to a central core, and having a base containing the transformer wherein movement of said actuator translates the core within the transformer to produce the error signal corresponding to the magnitude and direction of the translation of the core, a generally hollow cylindrical sleeve, enclosing said support member and each said miniature force sensor, forming a manually engageable surface, means for said sleeve to independently engage each said actuator, and means for positioning and returning said sleeve to a stable position and having elastic resistance to force in any direction whereby any said manual force applied to said sleeve translates said actuator to thus produce said error signal which is proportional to the magnitude and direction of said force.

3. The handle apparatus as recited in claims 1 or 2 wherein said means for positioning said sleeve and having elastic resistance to force comprises a spring diaphragm interposed between said base and said actuator of each said force sensor whereby any said manual force applied to said sleeve operates through each said spring diaphragm.

4. The handle apparatus as recited in claims 1 or 2 herein said means for said sleeve to engage the actuator of at least one said force sensor comprises a pin fixedly positioned perpendicularly to the desired axis of power-assist within said sleeve, and said actuator has an aperture adapted to receive said pin with slidable engagement whereby a force only in the direction of power-assist will translate said actuator.

5. The handle apparatus as recited in claims 1 or 2 wherein said apparatus includes one said force sensor corresponding to a device in which only one axis of power-assist is desired.

6. The handle apparatus as recited in claims 1 or 2 wherein said apparatus includes two said force sensors positioned perpendicularly to each other corresponding to a device in which two axes power-assist is desired.

7. The handle apparatus as recited in claims 1 or 2 wherein said apparatus incudes three said force sensors positioned mutually perpendicularly to each other corresponding to a device in which three axes of power-assist is desired.

* * * * *